United States Patent [19]

Paulik et al.

[11] Patent Number: 5,276,066
[45] Date of Patent: Jan. 4, 1994

[54] HALOGEN-FREE CYCLIC PHOSPHORUS-CONTAINING FLAME RETARDANT COMPOUNDS

[75] Inventors: Frank E. Paulik, St. Louis; Carol R. Weiss, Florissant, both of Mo.

[73] Assignee: Monsanto Company, St. Louis, Mo.

[21] Appl. No.: 963,780

[22] Filed: Oct. 20, 1992

[51] Int. Cl.$^5$ .............................................. C08G 18/14
[52] U.S. Cl. .................................... 521/108; 549/216; 524/108; 524/707; 106/18.15
[58] Field of Search .................... 521/108; 549/216; 524/108, 707; 106/18.15

[56] References Cited

U.S. PATENT DOCUMENTS

| | | | |
|---|---|---|---|
| 3,332,893 | 7/1967 | Birum et al. | 260/2.5 |
| 3,922,323 | 11/1975 | Reese et al. | 558/77 |
| 3,969,437 | 7/1976 | Shim | 558/83 |
| 4,034,141 | 7/1977 | Duffey et al. | 558/77 |
| 4,071,583 | 1/1978 | Hochenbleikner | 260/927 R |
| 4,073,767 | 2/1978 | Birum | 260/45.8 R |
| 4,139,476 | 2/1979 | Hancock | 252/8.1 |
| 4,351,779 | 9/1982 | Maier | 558/166 |
| 4,397,759 | 8/1983 | Hancock | 252/609 |
| 4,414,345 | 11/1983 | Rasberger | 524/108 |
| 5,099,056 | 3/1992 | Ha et al. | 558/166 |

FOREIGN PATENT DOCUMENTS 50-24395  3/1975  Japan ........................ 524/119

OTHER PUBLICATIONS

Derwent Abstract No. 48440 W/29 (1975); JP 50024395.
"Structure of Phosphorus Derivatives Containing A 1,3,2-Dioxaphospholane Ring" Ovchinnikov et al., Zhurnal Obshchei Khimii, vol. 48, No. 11, pp. 2424-2423, Nov., 1978.
"Synthesis of Cyclic Phosphorous Acid Esters By Transesterification", A. A. Oswald, Can. J. Chem., vol. 37 (1959) pp. 1498-1504.
"Cyclic Organophosphorous Compounds I. Synthesis and Infrared Spectral Studies of Cyclic Hydrogen Phosphites and Thiophosphites", A. Zwierzak, Can. J. Chem., vol. 45 (1967) pp. 250-2512.
"Synthesis of Trimethylene Hydrogen Phosphites" Nifant'ev et al. Zhurnal Obshchei Khimii, vol. 41, No. 11, pp. 2368-2371, Nov., 1971.
"Ein Neues Verfahren Zer Darstellung Von Aminomethylenphosphonsäuren" Krüger et al., Chemiker-Zeitung, 96, Jahrgang (1972), NR. 12, p. 691.
"The Direct Synthesis of α-Aminomethylphosphonic Acids, Mannich-Type Reactions with Orthophosphorous Acid" Moedritzer et al., J. Org. Chem. May 31, 1966, pp. 1603-1607.
"Synthesis of Aminodiphosphonates and Aminotriphosphonates" Petrov et al., J. Gen. Chem. USSR, 29, 1959, English translation pp. 587-560.

*Primary Examiner*—Maurice J. Welsh
*Attorney, Agent, or Firm*—Lawrence L. Limpus

[57] ABSTRACT

Certain (1,3,2-dioxaphosohorinanemethan) amine compounds, which are useful as halogen-free flame retardant compounds, are disclosed. The compounds are particularly useful in polyurethane compositions.

15 Claims, No Drawings

HALOGEN-FREE CYCLIC PHOSPHORUS-CONTAINING FLAME RETARDANT COMPOUNDS

BACKGROUND OF THE INVENTION

This invention relates to novel cyclic phosphorus-containing compounds and, in particular, to certain (1,3,2 - dioxaphosphorinanemethan) amine compounds which are useful as fire retardant materials.

Cyclic phosphorus compounds including dioxaphosphorinanes are known to be effective flame retardant compounds for various synthetic resin compositions. U.S. Pat. No. 4,073,767, to Birum, discloses cyclic phosphorus compounds which include phosphorinane rings which are taught to be useful as flame retardants for polyurethanes, polyesters and polyamides. In U.S. Pat. No. 4,397,750, to Hancock, certain cyclic phosphonate esters are shown to be useful flame retardants for polypropylene and other polyolefins.

This invention is directed to certain (1,3,2 - dioxaphosphorinanemethan) amine compounds which are novel compositions and which are particularly useful as halogen-free flame retardant materials for use in organic polymeric materials such as, for example, polyurethane foams, other compositions containing polyurethane and compositions containing polyesters, styrenic polymers, polyvinyl chloride, polyvinyl acetates or polycarbonates. These novel cyclic phosphorus compounds, when used in other polymeric materials provide advantages over the prior art by providing improved flame retardant characteristics such as low smoke and low smoulder without the presence of halogen atoms and, when they are used in foams, the compounds increase the load bearing capabilities of the foams.

SUMMARY OF THE INVENTION

The general formula for the novel (1,3,2-dioxaphosphorinanemethan) amine compounds of the invention is:

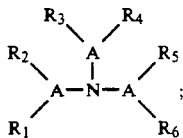

wherein A is:

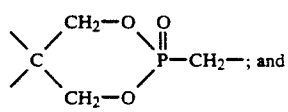

$R_1$, $R_2$, $R_3$, $R_4$, $R_5$, and $R_6$ are independently selected from the group consisting of hydrogen, alkyl groups having from 1 to 4 carbon atoms and aryl and substituted aryl groups having from 6 to 8 carbon atoms.

The invention also provides a process for the preparation of the novel (1,3,2-dioxaphosphorinanemethan) amine compounds comprising the steps of:

(a) reacting a normal-alcohol having from 4 to about 8 carbon atoms and paraformaldehyde with hexamethylenetetramine in the presence of a catalyst comprising an organic aliphatic carboxylic acid having from 2 to about 7 carbon atoms to produce a tris-alkoxymethanamine having the general formula:

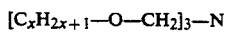

wherein X is a number from 4 to about 8;

(b) purifying the tris-alkoxymethanamine;

(c) adding phosphorus trichloride to a mixture of a 1,3-diol derivative and water and an organic solvent at a temperature of from about 10° C. to about 60° C. to produce a 5,5-di-substituted 1,3,2-dioxaphosphorinane-2-oxide having the general formula:

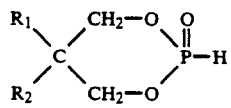

wherein $R_1$ and $R_2$ are independently selected from the group consisting of hydrogen, alkyl groups having from to 4 carbon atoms and aryl and substituted aryl groups having from 6 to 8 carbon atoms; (d) purifying the 5,5-di-substituted 1,3,2-dioxaphosphorinane-2-oxide; (e) reacting the tris-alkoxymethanamine and the 5,5-di-substituted 1,3,2-dioxaphosphorinane-2-oxide in an organic solvent with an acid catalyst to produce 5,5,5',5',5'',5''-substituted tris(1,3,2-dioxaphosphorinanemethan) amine 2,2',2''-trioxide having the general formula:

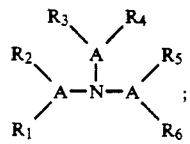

wherein A is:

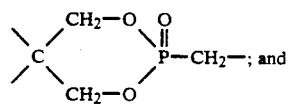

$R_1$, $R_2$, $R_3$, $R_4$, $R_5$, and $R_6$ are independently selected from the group consisting of hydrogen, alkyl groups having from 1 to 4 carbon atoms and aryl and substituted aryl groups having from 6 to 8 carbon atoms; and (f) purifying and drying the 5,5,5',5',5'',5''-substituted tris(1,3,2-dioxaphosphorinanemethan) amine 2,2',2''-trioxide.

Organic polymeric compositions containing the (1,3,2 - dioxaphosphorinanemethan) amine compounds of the invention which have improved fire retardant properties are also provided.

DESCRIPTION OF THE PREFERRED EMBODIMENTS

The novel (1,3,2 - dioxaphosphorinanemethan) amine compounds of the invention which are shown by the above general formula include 5,5,5',5',5'',5''-hexamethyl tris(1,3,2-dioxaphosphorinanemethan) amine 2,2',2''-trioxide; 5,5,5',5',5'',5''-hexaethyl tris(1,3,2-dioxaphosphorinanemethan) amine 2,2',2''-trioxide; 5,5,5',5'-tetramethyl, 5'',5''-diethyl tris(1,3,2-dioxaphosphorinanemethan) amine 2,2',2''-trioxide; 5,5-dimethyl, 5',5,-ditolyl, 5'',5''-diisobutyl tris(1,3,2-dioxaphosphorinanemethan) amine 2,2',2''-trioxide; and 5,5,5',5',5'',5''-hexatolyl tris(1,3,2-dioxaphosphorinanemethan) amine 2,2',2''-trioxide.

The invention also provides a process for the preparation of the novel (1,3,2-dioxaphosphorinanemethan) amine compounds comprising the steps of:

(a) reacting a normal-alcohol having from 4 to about 8 carbon atoms and paraformaldehyde with hexamethylenetetramine in the presence of a catalyst comprising an organic aliphatic carboxylic acid having from 2 to about 7 carbon atoms to produce a tris-alkoxymethanamine having the general formula:

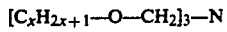

wherein X is a number from 4 to about 8;

(b) removing the water produced in step (a) to complete the reaction and removing the excess alcohol after the reaction is complete;

(c) purifying the tris-alkoxymethanamine by distillation or by washing with an alkaline wash, washing with water and filtering the tris-alkoxymethanamine;

(d) adding phosphorus trichloride to a mixture of a 1,3-diol derivative and water and an organic solvent at a temperature of from about 10° C. to about 60° C. to produce a 5,5-di-substituted 1,3,2-dioxaphosphorinane-2-oxide having the general formula:

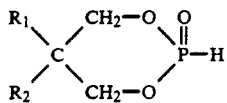

wherein $R_1$ and $R_2$ are independently selected from the group consisting of hydrogen, alkyl groups having from 1 to 4 carbon atoms and aryl and substituted aryl groups having from 6 to 8 carbon atoms;

(e) heating the 5,5-di-substituted 1,3,2-dioxaphosphorinane-2-oxide to remove hydrogen chloride, removing excess solvent and purifying the 5,5-di-substituted 1,3,2-dioxaphosphorinane-2-oxide;

(f) reacting the tris-alkoxymethanamine and the 5,5-di-substituted 1,3,2-dioxaphosphorinane-2-oxide in an organic solvent with an acid catalyst to produce 5,5,5',5',5'',5''-substituted tris(1,3,2-dioxaphosphorinanemethan) amine 2,2',2''-trioxide having the general formula:

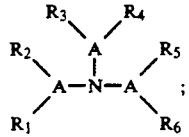

wherein A is:

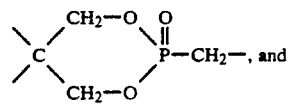

$R_1, R_2, R_3, R_4, R_5,$ and $R_6$ are independently selected from the group consisting of hydrogen, alkyl groups having from 1 to 4 carbon atoms and aryl and substituted aryl groups having from 6 to 8 carbon atoms; and (g) washing the 5,5,5',5',5'',5''-substituted tris(1,3,2-dioxaphosphorinanemethan) amine 2,2',2''-trioxide with a base, followed by filtering, washing with an alcohol and washing with water before drying.

The general reaction sequence for the preparation of the (1,3,2-dioxaphosphorinanemethan) amine compounds of the invention is:

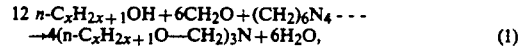
(1)

where X is a number between 4 and about 8;

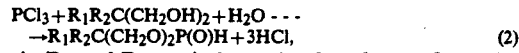
(2)

wherein $R_1$ and $R_2$ are independently selected from the group consisting of hydrogen, alkyl groups having from 1 to 4 carbon atoms and aryl and substituted aryl groups having from 6 to 8 carbon atoms; and

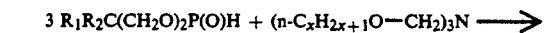

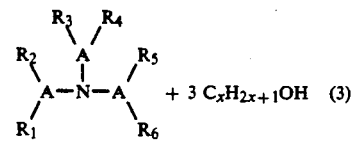
(3)

wherein A is:

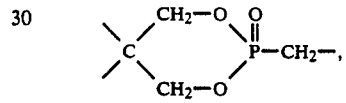

X is a number between 4 and about 8, and $R_1, R_2, R_3, R_4, R_5,$ and $R_6$ are independently selected from the group consisting of hydrogen, alkyl groups having from 1 to 4 carbon atoms and aryl and substituted aryl groups having from 6 to 8 carbon atoms. In addition, other elements such as nitrogen, oxygen and sulfur may be present.

In the first step of the process, a normal alcohol having from 4 to about 8 carbon atoms, paraformaldehyde and hexamethylenetetramine were reacted in the presence of a catalyst comprising an organic aliphatic carboxylic acid having from 2 to about 7 carbon atoms to produce an intermediate product, tris-alkoxymethanamine, as shown in Formula (1) above. An illustrative example of this reaction provides n-hexanol to react with the paraformaldehyde and hexamethylenetetramine to produce tris-hexoxymethanamine. The water produced during the reaction was removed as it was produced. Ammonia and formaldehyde, which react to produce hexamethylenetetramine, may be used in place of the hexamethylenetetramine in the reaction.

Several alcohols were used in the reaction. Normal alcohols having from 4 to about 8 carbon atoms are suitable and n-hexanol was preferred. Alcohols having less than four carbon atoms, lower than butanol, were unacceptable because of their high solubility in water. Secondary alcohols, except for cyclohexanol, do not perform well because they do not form a stable hemiformal. The formation of the hemiformals, necessary in this reaction to retain the formaldehyde in solution, requires the presence of an acid catalyst. Acetic acid was used as the catalyst; however, any organic carboxylic acid catalyst having from 2 to about 7 carbon atoms may be used. Inorganic acids were found to be unacceptable because they precipitate during the reaction and cause undesirable side reactions.

When butanol is used as the alcohol in the first step of this reaction, entrainment agents such as benzene, toluene or xylene are required to remove the water that is formed during the reaction. When n-hexanol, the preferred alcohol, and higher alcohols having up to about 8 carbon atoms, are used, no additional entrainment agents are needed and the process is simplified.

Since side reactions and formaldehyde losses occur at higher temperatures, it is preferred that the reaction take place within the boiling point range of 60° to 80° C., under a reduced pressure that is determined by the boiling point of the solvent-water azeotrope. Excessive boil-up rates must be avoided to prevent high losses of formaldehyde.

The tris-alkoxymethanamine produced in this first step of the reaction was purified by distillation or by washing using an alkaline wash such as, for example, aqueous ammonium hydroxide, to remove excess hexamethylenetetramine and formaldehyde. The alkaline wash was followed by a water wash, the water was removed and the tris-alkoxymethanamine was filtered. Any of the known procedures for washing a product and for removing the wash liquid may be used.

In the second step of the process, phosphorus trichloride was reacted with a 1,3-diol derivative in a mixture of the 1,3-diol derivative and water and a suitable organic solvent at a temperature of from about 10° C. to about 80° C., and preferably at a temperature of about 10° C. to about 60° C., and more preferably at a temperature of about 50° C., to produce an intermediate product, 5,5-di-substituted 1,3,2-dioxaphosphorinane-2-oxide. Suitable 1,3-diol derivatives include, for example, 1,3-propylene glycol, 1,3-isobutylene glycol and neopentyl glycol. Suitable organic solvents include benzene, monochlorobenzene, toluene, xylene and similar aromatic compounds which do not react with phosphorus trichloride. In this procedure, the phosphorus trichloride must be added to the slurry below the surface to prevent entrainment losses. The 5,5-di-substituted 1,3,2-dioxaphosphorinane-2-oxide was heated to remove hydrogen chloride and vacuum stripping was used to remove excess solvent.

The product, 5,5-di-substituted 1,3,2-dioxaphosphorinane-2-oxide, was purified. The product with lower molecular weight substituents may be distilled at a temperature within the range of from about 100° to about 140° C., preferably at a temperature of about 110° C., at a pressure of from about 0.1 mm. to about 5.0 mm. of mercury and the still bottoms may be recycled to increase yields and reduce waste. During distillation the still bottoms should be maintained at a temperature of approximately 140° C. or less. If the product has higher molecular weight substituents, other purification methods may be used. Air leaks must be minimized, by any known methods, during the distillation as exposure to air and moisture will cause decomposition of the 5,5-di-substituted 1,3,2-dioxaphosphorinane-2-oxide.

The first two steps of the process described above may easily be reversed in sequence to first produce the 5,5-di-substituted 1,3,2-dioxaphosphorinane-2-oxide and then to produce the tris-alkoxymethanamine. It is also contemplated that the two steps may be taken simultaneously, the two reactions may occur at the same time in separate vessels.

In the final step of the process, the phosphonate produced in the second step of the process, 5,5-di-substituted 1,3,2-dioxaphosphorinane2-oxide, was reacted with the amine produced in the first step, tris-alkoxymethanamine, in an organic solvent in the presence of a catalyst to produce 5,5,5',5',5'',5''-substituted tris(1,3,2-dioxaphosphorinanemethan) amine 2,2',2''-trioxide.

Any suitable organic solvent such as, for example, alcohols, toluene and xylene may be used. The phosphonate and the amine react at a temperature within the range of from about 20° C. to about 100° C. and the range of from about 40° C. to about 60° C. is preferred. A catalyst is required as the pure phosphonate will not readily react with the amine, even at 130° C., if a catalyst is not present. An acid catalyst is preferred; however, not all acids will catalyze the reaction. Acids which provided very little catalytic activity in the reaction included acetic and benzoic acids. The stronger acids such as, for example, phosphoric acid, phosphorous acid, toluenesulfonic acid and hydrochloric acid, provided more catalytic activity in the reaction. Hydrochloric acid was preferred as it catalyzed the reaction and provided higher yields at 50° C. Both higher and lower temperatures, compared to 50° C., appeared to reduce the yield.

The 5,5,5',5',5'',5''-substituted tris(1,3,2-dioxaphosphorinanemethan) amine 2,2',2''-trioxide was washed with a base and the material was filtered. The filtered material was washed with an alcohol and then with water before it was dried.

If the preferred raw materials are used in the process described above, in first step of the process n-hexanol was reacted with paraformaldehyde and hexamethylenetetramine to produce tris-hexoxymethanamine. In the second step of the process, phosphorus trichloride was reacted with neopentyl glycol in a mixture of neopentyl glycol and water to produce 5,5-dimethyl 1,3,2-dioxaphosphorinane-2-oxide. In the final step of the process the tris-hexoxymethanamine was reacted with the 5,5-dimethyl 1,3,2-dioxaphosphorinane-2-oxide to produce 5,5,5',5',5'',5''-hexamethyl tris(1,3,2-dioxaphosphorinanemethan) amine 2,2',2''-trioxide.

The following tables, Tables 1–4, illustrate the raw material requirements and the yields for each step of the process described above using the preferred raw materials and the overall yield for the principal raw materials. When other raw materials are used, such as other alcohols or acids as described above, the requirements shown below will change. In the tables, all parts and percents are by weight unless otherwise indicated. Each table illustrates the grams of the raw material used to produce 100 grams of the product of that step of the process.

TABLE 1

Production of Tris-Hexoxymethanamine

| Material | (GMs/100 GMs of Product) | Yield (%) |
|---|---|---|
| Hexamethylenetetramine | 10.4 | 93.7 |
| Paraformaldehyde | 14.2 | |
| n-Hexanol | 108.9 | |
| Acetic Acid | 0.15 | |
| Water (for the wash) | 150.0 | |
| Ammonium Hydroxide (28%) | 1.0 | |

TABLE 2

Production of 5,5-Dimethyl 1,3,2-Dioxaphosphorinane-2-Oxide

| Material | (GMs/100 GMs of Product) | Yield (%) |
|---|---|---|
| Phosphorus Trichloride | 99.64 | 92.0 |

TABLE 2-continued

Production of 5,5-Dimethyl 1,3,2-Dioxaphosphorinane-2-Oxide

| Material | (GMs/100 GMs of Product) | Yield (%) |
|---|---|---|
| Neopentyl Glycol | 75.36 | 92.0 |
| Water | 13.05 | |
| Monochlorobenzene | 75.00 | |

TABLE 3

Production of 5,5,5',5',5'',5''-Hexamethyl Tris(1,3,2-Dioxaphosphorinanemethan)Amine 2,2',2''-Trioxide

| Material | (GMs/100 GMs of Product) | Yield (%) |
|---|---|---|
| 5,5-Dimethyl 1,3,2-Dioxaphosphorinane-2-Oxide | 97.2 | 92.0 |
| Tris-Hexoxymethanamine | 77.5 | 92.0 |
| n-Hexanol | 150.0 | |
| HCL (Anhydrous) | 0.5 | |
| Water | 250.0 | |
| Caustic | 4.0 | |

TABLE 4

Overall Yield

| Phosphorus Trichloride | 84.6% |
|---|---|
| Neopentyl Glycol | 84.6% |
| Hexamethylenetetramine | 86.0% |

The invention is further illustrated by the following examples in which all of the parts and percents are by weight unless otherwise indicated.

EXAMPLE I

Preparation of Tris-n-Hexoxymethanamine

A nitrogen purged reaction flask, equipped with an agitator, condenser, Dean-Stark trap to remove water, vacuum receiver and vacuum source, was charged with 491 grams of n-hexanol (20% excess), 63.9 grams of 95% paraformaldehyde (1% excess), 46.8 grams of hexamethylenetetramine and 1.35 grams of acetic acid catalyst. After stirring for 30 minutes, the reactor contents were slowly heated to a temperature between about 70° C. and about 80° C. when a vacuum was slowly applied until vapors began to distill at a steady rate. The vapor was passed through the condenser and the condensate was sent to the Dean-Stark trap which removed the water layer and returned the organic material to the reactor. The batch was held at the elevated temperature while the pressure was gradually lowered to continue removing the water of reaction. After about 6 hours, when the rate of water removal has slowed appreciably, the reaction conditions were maintained for another 2 hours, or until the water removal almost stops. The excess alcohol was then removed by vacuum stripping by lowering the reactor pressure to about 20 mm. of mercury while the temperature was maintained between about 70° C. and about 80° C. The reactor batch was then cooled to about 5° C., the vacuum was dropped by the addition of nitrogen and the reactor was charged with 225 grams of water and 4.5 grams of 28% aqueous ammonia. After stirring for about 30 minutes, agitation was stopped and the water layer was removed. The reactor contents were then washed two more times with 225 milliliter portions of water. After the washing was completed, the remaining water was stripped from the batch by gradually reducing the reactor pressure to about 20 mm. of mercury and then heating the reactor to a temperature between about 70° C. and about 80° C. and holding the pressure and temperature for about 30 minutes. The reactor contents were then cooled and the vacuum dropped by the addition of nitrogen. The product was about 450 grams of tris-n-hexoxymethanamine.

EXAMPLE II

Preparation of 5,5-Dimethyl 1,3,2-Dioxaphosphorinane-2-Oxide

A nitrogen purged, glass reaction flask was charged with 226.2 grams of monochlorobenzene, 39 grams of water and 226.2 grams of neopentyl glycol. During a period of about 3 hours, 298.8 grams of phosphorus trichloride were added. During the first one-third of the addition, the reaction is exothermic and the batch was cooled to maintain the temperature between about 40° C. and about 50° C. After about one-third of the phosphorus trichloride was added, hydrogen chloride gas evolved at a substantial rate and external cooling was no longer necessary as the evolution of hydrogen chloride gas is endothermic. The hydrogen chloride gas was sent to a water scrubber. The reactor contents were kept at a temperature between about 40° C. and about 50° C. by heating the reactor and the addition of the phosphorus trichloride was continued at a rate that prevented foaming. After the addition of the phosphorus trichloride was completed, the temperature of the batch was raised to about 110° C. at a rate slow enough to prevent excessive foaming as additional hydrogen chloride gas was eliminated. The batch was held at about 110° C. for about 30 minutes before vacuum stripping was started by gradually reducing the reactor pressure to between about 20 mm. and 25 mm. of mercury. Vacuum stripping was continued until monochlorobenzene ceased to distill under these conditions. The remaining material was then vacuum distilled at a temperature between about 110° C. and about 130° C. and at a pressure between about 0.1 mm. and 2.0 mm. of mercury, with only a small forerun, to yield 300 grams of 5,5-dimethyl 1,3,2-dioxaphosphorinane-2-oxide.

EXAMPLE III

The Preparation of 5,5,5',5',5'',5''-Hexamethyl Tris(1,3,2-Dioxaphosphorinanemethan)amine 2,2',2''-Trioxide A glass lined reactor was charged with 35 kilograms of tris-n-hexoxymethanamine and 45 kilograms of n-hexanol. The agitator was started and the reactor was purged with nitrogen and sealed before 225 grams of anhydrous hydrochloric acid were added under the surface of the liquid through a dip tube. The reactor was heated to about 50° C. and 43.8 kilograms of molten (about 55° C.) 5,5-dimethyl 1,3,2-dioxaphosphorinane-2-oxide were added during a period of from about 2 to about 4 hours while cooling the batch to maintain a temperature between about 50° C. and about 55° C. After the addition, the batch was held at a temperature between about 50° C. and about 55° C. for 1 hour. After the reaction was complete, 45 kilograms of water and 1.8 kilograms of 50% caustic were added to the reactor. The temperature was reduced to a temperature between about 35° C. and about 40° C. and th batch was stirred for about 30 minutes. The pH of the batch was then measured to assure that the batch was slightly basic and, if not, additional caustic should be added. The batch was filtered, washed with 22.5 kilograms of n-hexanol and washed with 67.5 kilograms of water. The solid product was vacuum dried at a temperature of about 95° C. and at a pressure of about 10 mm. of mercury to yield about 45 kilograms of 5,5,5',5',5'',5''-hexamethyl tris(1,3,2-dioxaphosphorinanemethan)amine 2,2',2''-trioxide.

In the examples below the following flame retardant additives were used:

(a) XPM-1000, XPM-1000 produced by Monsanto Company, 5,5,5',5',5'',5''-hexamethyl tris(1,3,2-dioxaphosphorinanemethan)amine 2,2',2''-trioxide;
(b) A-100, Antiblaze 100 produced by Albright and Wilson Americas, Inc., Tetrakis(2-chloroethyl)-2,2-bis(chloromethyl)propylene diphosphate;
(c) C22R, Phosgard C22R which was produced by Monsanto Company, α-(2-chloroethyl) -ω-[[(2-chloroethoxy) (2chloroethyl) phosphinyl]oxy] poly-[oxy[(2-chloroethoxy) phosphinylidene]ethylidene];
(d) T-101, Thermolin 101 which was produced by Olin Corp., Tetrakis(2-chloroethyl) ethylene diphosphate;
(e) CEF, Fyrol CEF produced by Akzo Chemicals, Inc., Tris(2-chloroethyl) phosphate;
(f) T23-P, Firemaster T23-P produced by Great Lakes Chemical Company, Tris 2,3-dibromopropyl phosphate.

In the examples below the following materials were used:

(a) G30-56, oxypropylated polyether triol (MW=3000) sold by Olin Corp.;
(b) Niax 11-27, polyol sold by Arco Chemical Co.;
(c) Niax 34-38, polyol was sold by Arco Chemical Co.;
(d) Multranol 4034, sucrose based polyol sold by Miles, Inc.;
(e) Dabco 33LV, triethylene diamine (33%) in dipropylene glycol sold by Air Products and Chemicals, Inc.;
(f) Dabco R-8020, 20% triethylene diamine / 80% dimethylethanolamine sold by Air Products and Chemicals, Inc.;
(g) Diethanol Amine;
(h) E-9400, amine catalyst;
(i) NEM, amine catalyst;
(j) L-5720, silicon surfactant sold by Union Carbide Corporation;
(k) DC- surfactant sold by Dow Corning Corporation;
(l) T-9, stannous octoate;
(m) T-12, dibutyltin dilaurate;
(n) TDI (80/20), Toluene diisocyante;
(o) Mondur MR, polymeric MDI (diisocyanatodiphenylmethane) sold by Miles, Inc.;
(p) Freon II, monofluorotrichloromethane sold by E. I. duPont de Nemours and Company, Inc.

EXAMPLE IV

Procedure to Prepare Hand Mixed Formulations for Flexible Foam

Hand mixed laboratory pours were made into a box (45.7 cm. × 30.5 cm. × 25.4 cm. (free rise)) with a renewable liner such as kraft paper. The components of the formulation are identified in Table IV below, shown as parts by weight in relation to 100 parts by weight of the polyol. The polyol and water were premixed for a period of about 5 seconds at a mixer speed of 1700 rpm. The amine, the silicone surfactant and the flame retardant additive were added to the polyol/water mixture and mixed vigorously at a mixer speed of about 1700 rpm. for about 15 seconds. During the mixing, the catalyst was added to the mixture one drop at a time. At the end of the 15 seconds, mixing was continued as the isocyanate was added. After an additional 5 seconds of mixing, the mixture was poured into the box and allowed to cure for 24 hours. The cured foam was tested for physical and flame retardant properties in accordance with the following test methods, and the results are shown in Table IV:

| California Technical Bulletin 117, Section A, Part I; | |
|---|---|
| ASTM D3574-86, | Test A - Density Test, |
| | Test C - Compressive Force Deflection Test, |
| | Test G - Air Flow Test; |
| ASTM 1692-74, | Horizontal Burn; |
| ASTM D2813, | Oxygen Index |
| ASTM D3806, | 2 Foot (50.8 cm.) Tunnel; and |
| ISO844-1985, | Compressive Strength Parallel to the Direction of Foam Rise. |

In Table IV the column designated 25%CLD provides the results of the compressive load deflection test in which the force necessary to compress the foam 25% is measured.

TABLE IV 25.6 Kg/m³ Flexible Foam Formulation

| Component Identification | | Parts/100 Parts Polyol |
|---|---|---|
| Polyol | G30-56 | 100 |
| Blowing Agent | Water | 4.5 |
| Amine | Dabco 33LV | 0.52 |
| Silicone Surfactant | L5720 | 1.25 |
| Tin Catalyst | T-9 | 0.16 |
| Isocyanate | TDI (80/20) | 59 |
| Flame Retardant Additive | | 18 |

| | Test Results | | | | | |
|---|---|---|---|---|---|---|
| | | Air | California 117 | | | |
| Flame Retardant Additive | 25% CLD (KPa) | Flow (liter/sec) | Length (cm) | After-flame (sec) | ASTM 1692-74 (mm.) | (mm/sec.) |
| XPM-1000 | 4.3 | 2.6 | 7.4 | 0.7 | 80 | 1.50 |
| A-100 | 3.2 | 1.6 | 7.1 | 0.0 | 80 | 1.64 |
| T-101 | 2.9 | 2.3 | 7.6 | 0.2 | 64 | 1.25 |
| T23-P | 3.4 | 2.1 | | | 47 | 1.52 |
| CEF | 2.6 | 2.7 | | | 80 | 1.23 |
| Control | 4.1 | 1.8 | 27.9 | 9.0 | | |

EXAMPLE V

Procedure to Prepare Hand Mixed Formulations for Flexible Foam

The procedure of Example IV was repeated using different ratios for the components of the formulation to produce a flexible foam having a different density. In addition to using water as the blowing agent, a Freon ® blowing agent, a produce of E. I. duPont de Nemours & Company, Inc., was added to the formulation after the addition of the catalyst. After the addition of the Freon, the weight of the formulation was measured to allow for correction of any weight loss resulting from evaporation. The cured foam was tested for its resistance to compressive forces in accordance with the test methods listed in Example IV. The components of the formulation and results of the tests are shown in Table V. In Table V the column designated 25%CLD provides the results of the compressive load deflection test in which the force necessary to compress the foam 25% is measured. The "sag factor" is the compressive load necessary to compress the foam 65% of its height divided by the compressive load necessary to compress the foam 25% of its height.

TABLE V

| 19.2 Kg/m³ Flexible Foam Formulation | | |
|---|---|---|
| Component Identification | | Parts/100 Parts Polyol |
| Polyol | G30-56 | 100 |
| Blowing Agent | Freon II | 7 |
| Blowing Agent | Water | 5 |
| Amine | E-9400 | 0.12 |
| Amine | NEM | 0.5 |
| Silicone Surfactant | L5720 | 1.4 |
| Tin Catalyst | T-9 | 0.12 |
| Isocyanate | TDI (80/20) | 68 |
| Flame Retardant Additive | | 14 |

| | Test Results | |
|---|---|---|
| Flame Retardant Additive | 25% CLD (KPa) | Sag Factor |
| XPM-1000 | 4.3 | 2.38 |
| A-100 | 3.0 | 1.38 |
| T-101 | 2.8 | 1.74 |

EXAMPLE VI

Procedure to Prepare Hand Mixed Formulations for Flexible Foam

The procedure of Example IV was repeated using different ratios for the components of the formulation, including a mixture of two polyols, to produce a high resilience flexible foam. The cured foam was tested for physical and flame retardant properties in accordance with the test methods listed in Example IV. The components of the formulation and the results of the tests are shown in Table VI. The column under ASTM 1692-74 titled "SE" indicates whether the formulation was self-extinguishing.

TABLE VI

| High Resilience Flexible Foam Formulation | | |
|---|---|---|
| Component Identification | | Parts/100 Parts Polyol |
| Polyol | Niax 11-27 | 50 |
| Polyol | Niax 34-38 | 50 |
| Blowing Agent | Distilled Water | 3 |
| Amine | Dabco 33LV | 0.4 |
| Amine | Diethanol Amine | 0.8 |
| Silicone Surfactant | L5720 | 1.0 |
| Tin Catalyst | T-12 | 0.06 |
| Isocyanate | TDI (80/20) | 36 |
| Flame Retardant Additive | | 9 |

| | Test Results | | | | |
|---|---|---|---|---|---|
| Flame Retardant Additive | 25% CLD (KPa) | Air Flow (liter/sec) | Density (Kg/m³) | ASTM 1692-74 (mm.) | (mm/sec.) | SE |
| XPM-1000 | 15.2 | 0.7 | 41.6 | 26 | 0.81 | Y |
| A-100 | 10.2 | 0.5 | 35.2 | 27 | 1.09 | Y |
| T-101 | 10.9 | 0.7 | 36.8 | 27 | 0.84 | Y |
| Control | 9.2 | 0.6 | 35.2 | 125 | 1.25 | N |

EXAMPLE VII

Procedure to Prepare Hand Mixed Formulations for Rigid Foam

Hand mixed laboratory pours were made into a box (33 cm. × 33 cm. × 25.4 cm.) with a renewable liner such as kraft paper. The components of the formulation are identified in Table VII below as parts by weight in relation to 100 parts by weight of the polyol. The polyol and water wer premixed for a period of about 10 seconds at a mixer speed of 1700 rpm. The amine, the silicone surfactant and the flame retardant additive were added to the polyol/water mixture and mixed vigorously at a mixer speed of about 1700 rpm. for about 20 seconds. A Freon ® blowing agent, a product of E. I. duPont de Nemours & Company, Inc., was added with weight checks after addition and after mixing to allow corrections to be made for weight loss from evaporation. Mixing was continued as the isocyanate was added. After an additional 35 seconds of mixing, the mixture was poured into the box. The foam was allowed to cure for 48 hours. The cured foam was tested for physical and flame retardant properties in accordance with the test methods set out in Example IV and the results are shown in Table VII.

TABLE VII

| Rigid Foam Formulation | | |
|---|---|---|
| Component Identification | | Parts/100 Parts Polyol |
| Polyol | Multranol 4034 | 100 |
| Blowing Agent | Distilled Water | 1 |
| Blowing Agent | Freon II | 30 |
| Amine | Dabco R-8020 | 3 |
| Silicone Surfactant | DC-193 | 1.6 |
| Isocyanate | Mondur MR | 140 |
| Flame Retardant Additive | | 20 |

| | Test Results | | |
|---|---|---|---|
| Flame Retardant Additive | Compressive Strength (KPa) | Density (Kg/m³) | O₂ Index (%) |
| XPM-1000 | 190.2 | 2.6 | 23.2 |
| C22R | 241.8 | 1.6 | 24.3 |
| CEF | 235.6 | 2.7 | 23.7 |
| Control | 208.1 | 1.8 | 20.7 |

| | Test Results | | | |
|---|---|---|---|---|
| Flame Retardant Additive | 2 Foot (50.8 cm) Tunnel | | ASTM 1692-74 | |
| | (cm) | (% Trans.) | (mm.) | (mm/sec.) |
| XPM-1000 | 33 | 6 | 36 | 1.13 |
| C22R | 30.5 | 3 | 21 | 0.78 |
| CEF | 33 | 6 | 38 | 1.06 |
| Control | 40.6 | 12 | 125 | 3.29 |

Dimensional Stability (% Change in Volume at 60° C. and 95% Relative Humidity)

| | XPM-1000 | C22R | CEF | Control |
|---|---|---|---|---|
| 3 Days | 1.9% | 5.9% | 4.8% | 4.4% |
| 8 Days | 1.1% | 5.9% | 6.0% | 4.0% |
| 10 Days | 1.1% | 5.9% | 5.5% | 4.0% |
| 15 Days | 1.2% | 6.3% | 5.7% | 4.0% |

While certain preferred embodiments of the invention have been illustrated and described herein, it is to be understood that the invention is not limited thereby and that the invention may be variously practiced within the scope of the following claims.

We claim:

1. A compound having the formula:

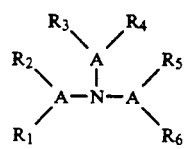

wherein A is:

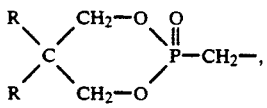

R is any one of $R_1$ to $R_6$, and $R_1$, $R_2$, $R_3$, $R_4$, $R_5$, and $R_6$ are independently selected from the group consisting of hydrogen, alkyl groups having from 1 to 4 carbon atoms and aryl and substituted aryl groups having from 6 to 8 carbon atoms and wherein the compound is a solid at ambient temperature.

2. The compound of claim 1 wherein $R_1$, $R_2$, $R_3$, $R_4$, $R_5$, and $R_6$ are independently selected from the group consisting of hydrogen and alkyl groups having from 1 to 4 carbon atoms.

3. The compound of claim 2 wherein $R_1$, $R_2$, $R_3$, $R_4$, $R_5$, and $R_6$ are methyl.

4. The compound of claim 1 wherein $R_1$, $R_2$, $R_3$, $R_4$, $R_5$, and $R_6$ are each independently selected from the group consisting of hydrogen and aryl and substituted aryl groups having from 6 to 8 carbon atoms.

5. The compound 5,5,5',5',5'',5''-hexamethyl tris(1,3,2-dioxaphosphorinanemethan)amine 2,2',2''-trioxide having the formula:

wherein A is:

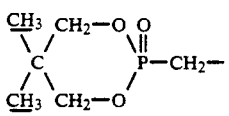

and wherein the compound is a solid at ambient temperature.

6. A composition of matter comprising an organic polymeric material and a fire retardant amount of a compound having the formula:

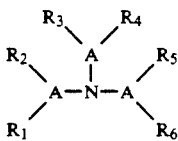

wherein A is:

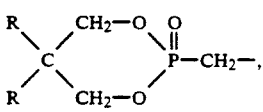

R is any one of $R_1$ to $R_6$, and $R_1$, $R_2$, $R_3$, $R_4$, $R_5$, and $R_6$ are independently selected from the group consisting of hydrogen, alkyl groups having from 1 to 4 carbon atoms and aryl and substituted aryl groups having from 6 to 8 carbon atoms and wherein the compound is a solid at ambient temperature.

7. The composition of matter of claim 6 wherein the organic polymeric material is selected from the group consisting of polyurethane foams, other polyurethane containing compositions, and compositions containing polyesters, styrenic polymers, polyvinyl chloride, polyvinyl acetates or polycarbonates.

8. The composition of matter of claim 7 wherein the organic polymeric material is a polyurethane foam.

9. The composition of matter of claim 6 wherein $R_1$, $R_2$, $R_3$, $R_4$, $R_5$, and $R_6$ are each independently selected from the group consisting of hydrogen and alkyl groups having from 1 to 4 carbon atoms.

10. The composition of matter of claim 9 wherein $R_1$, $R_2$, $R_3$, $R_4$, $R_5$, and $R_6$ are methyl.

11. The composition of matter of claim 6 wherein $R_1$, $R_2$, $R_3$, $R_4$, $R_5$, and $R_6$ are each independently selected from the group consisting of hydrogen and aryl and substituted aryl groups having from 6 to 8 carbon atoms.

12. A composition of matter comprising a polyurethane foam and a fire retardant amount of 5,5,5',5',5'',5''-hexamethyl tris(1,3,2-dioxaphosphorinanemethan) amine 2,2',2''-trioxide having the formula:

wherein A is:

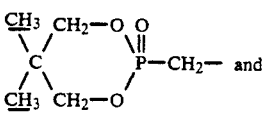

wherein the 5,5,5',5',5'',5''-hexamethyl tris(1,3,2-dioxaphosphorinanemethan) amine 2,2',2''-trioxide is a solid at ambient temperature.

13. A process for the production of compounds having the formula:

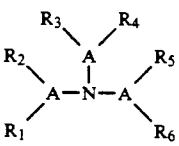

wherein A is:

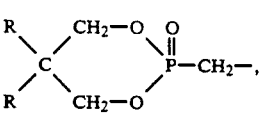

R is any one of $R_1$ to $R_6$, and $R_1$, $R_2$, $R_3$, $R_4$, $R_5$, and $R_6$ are independently selected from the group consisting of hydrogen, alkyl groups having from 1 to 4 carbon atoms and aryl and substituted aryl groups having from 6 to 8 carbon atoms, comprising the steps of:
(a) reacting a normal alcohol having from 4 to about 8 carbon atoms and paraformaldehyde with hexamethylenetetramine in the presence of a catalyst comprising an organic aliphatic carboxylic acid having from 2 to about 7 carbon atoms to produce a tris-alkoxymethanamine having the general formula:

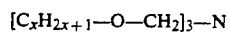

wherein X is a number from 4 to about 8;

(b) purifying the tris-alkoxymethanamine;
(c) adding phosphorus trichloride to a mixture of a 1,3-diol derivative and water and an organic solvent at a temperature of from about 10° C. to about 60° C. to produce a 5,5-di-substituted 1,3,2-dioxaphosphorinane-2-oxide having the general formula:

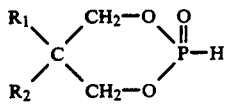

wherein $R_1$ and $R_2$ are independently selected from the group consisting of hydrogen, alkyl groups having from 1 to 4 carbon atoms and aryl and substituted aryl groups having from 6 to 8 carbon atoms;
(d) purifying the 5,5-di-substituted 1,3,2-dioxaphosphorinane-2-oxide;
(e) reacting the tris-alkoxymethanamine and the 5,5-disubstituted 1,3,2-dioxaphosphorinane-2-oxide in an organic solvent with an acid catalyst to produce 5,5,5',5',5'',5''-substituted tris(1,3,2-dioxaphosphorinanemethan) amine 2,2',2''-trioxide having the general formula:

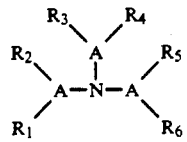

wherein A is:

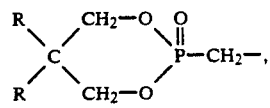

R is any one of $R_1$ to $R_6$, and $R_1$, $R_2$, $R_3$, $R_4$, $R_5$, and $R_6$ are independently selected from the group consisting of hydrogen, alkyl groups having from 1 to 4 carbon atoms and aryl and substituted aryl groups having from 6 to 8 carbon atoms; and
(f) purifying and drying the 5,5,5',5',5'',5''-substituted tris(1,3,2-dioxaphosphorinanemethan) amine 2,2',2''-trioxide.

14. The process of claim 13 for the production of a compound having the formula:

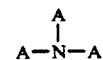

wherein A is:

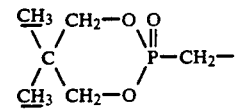

comprising the steps of:
(a)
(a) reacting a normal alcohol having from 4 to about 8 carbon atoms and paraformaldehyde with hexamethylenetetramine in the presence of a catalyst comprising an organic aliphatic carboxylic acid having from 2 to about 7 carbon atoms to produce a tris-alkoxymethanamine having the general formula:

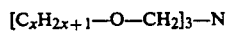

wherein X is a number from 4 to about 8;
(b) purifying the tris-alkoxymethanamine;
(c) adding phosphorus trichloride to a mixture of a neopentyl glycol and water and an organic solvent at a temperature of from about 10° C. to about 60° C. to produce 5,5-dimethyl 1,3,2-dioxaphosphorinane-2-oxide having the formula:

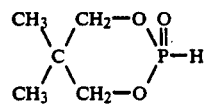

(d) purifying the 5,5-di-substituted 1,3,2-dioxaphosphorinane-2-oxide;
(e) reacting the tris-alkoxymethanamine and the 5,5-dimethyl 1,3,2-dioxaphosphorinane-2-oxide in an organic solvent with an acid catalyst to produce 5,5,5',5',5'',5''-hexamethyl tris(1,3,2-dioxaphosphorinanemethan) amine 2,2',2''-trioxide having the formula:

wherein A is:

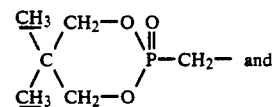

(f) purifying and drying the 5,5,5',5',5'',5''-hexamethyl tris(1,3,2-dioxaphosphorinanemethan) amine 2,2',2''-trioxide.

15. The process of claim 14 for the production of a compound having the formula:

wherein A is:

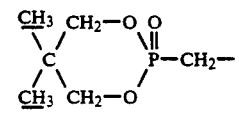

comprising the steps of:
(a) reacting a normal alcohol having from 4 to about 8 carbon atoms and paraformaldehyde with hexamethylenetetramine in the presence of a catalyst comprising an organic aliphatic carboxylic acid having from 2 to about 7 carbon atoms to produce a tris-alkoxymethanamine having the general formula:

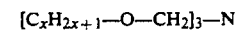

wherein X is a number from 4 to about 8;

(b) removing the water produced in step (a) to complete the reaction and removing the excess alcohol after the reaction is complete;

(c) purifying the tris-alkoxymethanamine by washing with an alkaline wash, washing with water and filtering;

(d) adding phosphorus trichloride to a mixture of neopentyl glycol and water and an organic solvent at a temperature of from about 10° C. to about 60° C. to produce a 5,5-dimethyl 1,3,2-dioxaphosphorinane-2-oxide having the formula:

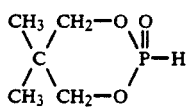

(e) heating the 5,5-dimethyl 1,3,2-dioxaphosphorinane-2-oxide to remove hydrogen chloride, removing excess solvent and purifying the 5,5-dimethyl 1,3,2-dioxaphosphorinane-2-oxide;

(f) reacting the tris-alkoxymethanamine and the 5,5-dimethyl 1,3,2-dioxaphosphorinane-2-oxide in an organic solvent with an acid catalyst to produce 5,5,5',5',5'',5''-hexamethyl tris(1,3,2-dioxaphosphorinanemethan) amine 2,2',2''-trioxide having the formula:

wherein A is:

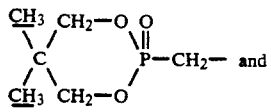 and (g) washing the 5,5,5',5',5'',5''-hexamethyl tris(1,3,2-dioxaphosphorinanemethan) amine 2,2',2''-trioxide with a base, followed by filtering, washing with an alcohol and washing with water before drying.

* * * * *